US006787681B2

United States Patent
Murakami et al.

(10) Patent No.: US 6,787,681 B2
(45) Date of Patent: Sep. 7, 2004

(54) ADHESIVE SHEET FOR APPLICATION ON SKIN AND PROCESS FOR PRODUCTION THEREOF

(75) Inventors: Yoshihide Murakami, Ibaraki (JP); Katsuhiro Okada, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 82 days.

(21) Appl. No.: 10/317,076

(22) Filed: Dec. 12, 2002

(65) Prior Publication Data

US 2003/0124343 A1 Jul. 3, 2003

(30) Foreign Application Priority Data

Dec. 28, 2001 (JP) ..................................... P2001-400671

(51) Int. Cl.$^7$ ................................................ A61F 13/00
(52) U.S. Cl. ........................... 602/57; 602/602; 602/54; 602/58
(58) Field of Search ................................ 424/443–449; 602/41–59; 128/888, 889; 604/304–308; 428/315, 317, 507

(56) References Cited

U.S. PATENT DOCUMENTS 4,909,244 A    3/1990    Quarfoot et al.
5,543,151 A  * 8/1996    Shirai et al. ................. 424/448
5,674,346 A   10/1997    Kundel
5,709,651 A  * 1/1998    Ward ............................ 602/57
6,461,644 B1 * 10/2002   Jackson et al. ............. 424/499

FOREIGN PATENT DOCUMENTS

| EP | 0 531 938 A1 | 3/1993 |
| EP | 0 601 463 A1 | 6/1994 |
| EP | 0 624 635 A2 | 11/1994 |
| EP | 1 013 734 A1 | 6/2000 |
| EP | 1 181 942 A2 | 2/2002 |
| EP | 1 184 039 A2 | 6/2002 |
| WO | WO 91/01706 A1 | 2/1991 |

OTHER PUBLICATIONS

European Search Report dated Sep. 25, 2003.

* cited by examiner

Primary Examiner—Kim M. Lewis
(74) Attorney, Agent, or Firm—Sughrue Mion, PLLC

(57) ABSTRACT

An adhesive sheet for application on skin contains a supporting film, an elastomer film and an adhesive layer laminated in this order, wherein the adhesive layer mainly contains an acrylic polymer and both the adhesive layer and the supporting film contain a component compatible with the acrylic polymer and liquid or pasty at ordinary temperature.

18 Claims, 1 Drawing Sheet

ADHESIVE SHEET FOR APPLICATION ON SKIN AND PROCESS FOR PRODUCTION THEREOF

FIELD OF THE INVENTION

The present invention relates to an adhesive sheet for application on skin containing an elastomer film and a process for the production thereof. More particularly, the invention relates to an adhesive sheet for application on skin which exhibits both an excellent workability during production and an excellent handleability during sticking and is so flexible so as to follow thoroughly the contour of even bent adherend after sticking and a process for the production thereof.

BACKGROUND OF THE INVENTION

As the substrate (The "substrate" acts to support an adhesive layer) for an adhesive sheet which is applied to a movable and flexible curved surface such as skin there has heretofore been often used an elastomer film such as polyurethane having a high rubber elasticity to allow the adhesive sheet to follow the contour of the skin. Further, such an adhesive sheet is required to have a high moisture permeability and flexibility for the purpose of minimizing a feeling of physical disorder during sticking and skin irritation such as rash caused by prevention of perspiration. To this end, the substrate to be incorporated in the adhesive sheet for application on skin needs to have a low stress and an extremely low thickness. An elastomer film having a modulus of not greater than 10 N/mm$^2$ at 50% elongation and a thickness of not greater than 70 μm has been widely used.

Such an adhesive sheet containing an elastomer film has a low stress and an extremely low thickness as mentioned above and thus naturally exhibits deteriorated workability during production and deteriorated handleability in use. In order to solve this problem, an adhesive sheet having a three-layer structure containing an adhesive layer, an elastomer film and a supporting film obtained by tentatively supporting an elastomer film on a film such as synthetic resin and paper (hereinafter referred to as "supporting film") for the purpose of reinforcing the elastomer film has been proposed. The adhesive sheet is designed such that the supporting film can be peeled off and removed from the elastomer film after the sticking of the adhesive layer on the desired site during the use of the adhesive sheet.

The adhesive sheet for application on skin as mentioned above preferably has as low adhesion between the elastomer film and the supporting film as possible from the standpoint of ease of peeling of the supporting film off the elastomer film in use. However, when the adhesion between the elastomer film and the supporting film is too low, it is disadvantageous in that the elastomer film and the supporting film are peeled off each other during production. Accordingly, such an adhesive sheet is required to have an adhesion between the elastomer film and the supporting film that gives well-balanced handleability in use and workability during production. However, such an adhesion has an extremely narrow tolerance and thus can be difficultly attained invariably.

SUMMARY OF THE INVENTION

The invention has been worked out in the light of these problems. The invention is intended to provide an adhesive sheet for application on skin excellent in workability and handleability which exhibits so high an adhesivity that the elastomer film and the supporting film cannot be easily peeled off each other during production but shows a drop of adhesion between the elastomer film and the supporting film to allow the supporting film to be easily removed from the elastomer film during use and a process for the production thereof.

The inventors made extensive studies of solution to the aforementioned problems. As a result, it was found that when a component compatible with a specific adhesive and liquid or pasty at ordinary temperature is present in the supporting film after production of the adhesive sheet, there occurs a proper drop of the adhesion between the elastomer film and the supporting film that gives excellency in both producibility and handleability in use. The invention has thus been worked out.

The invention provides an adhesive sheet for application on skin which contains an adhesive layer and a laminated film containing an elastomer film having provided on one side thereof a supporting film, the adhesive layer being formed on the elastomer film side of the laminated film, wherein the adhesive layer mainly contains an acrylic polymer and both the adhesive layer and the supporting film contain a component compatible with the acrylic polymer and liquid or pasty at ordinary temperature.

The invention also provides a process for the production of an adhesive sheet for application on skin, which adhesive sheet contains an adhesive layer and a laminated film containing an elastomer film having provided on one side thereof a supporting film, the adhesive layer being formed on the elastomer film side of the laminated film, wherein the adhesive layer mainly contains an acrylic polymer and both the adhesive layer and the supporting film contain a component compatible with the acrylic polymer and liquid or pasty at ordinary temperature, which process for the production of the adhesive sheet contains applying an adhesive mainly containing the acrylic polymer containing the component compatible with the acrylic polymer and liquid or pasty at ordinary temperature to the laminated film, and then allowing a part of the liquid or pasty component contained in the adhesive to move toward the supporting film so that it is present therein.

Figure 1:
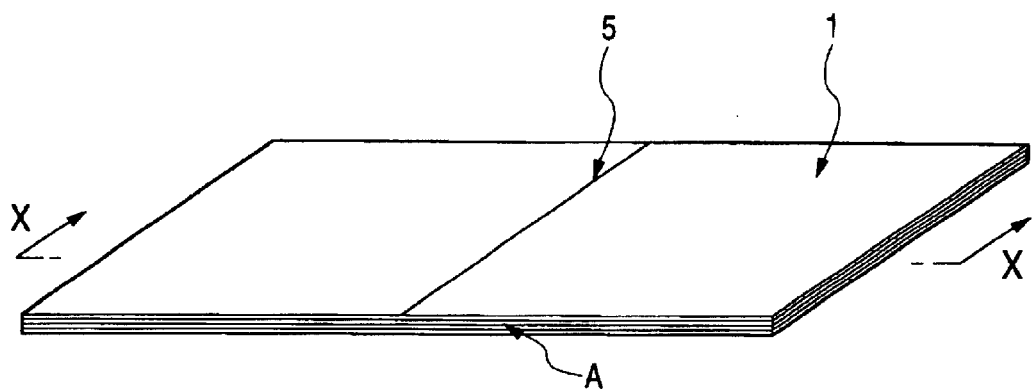
FIG. 1 is an oblique perspective view illustrating an embodiment of the adhesive sheet for application on skin of the invention.

Description of the Reference Numerals and Signs

1 Release paper
2 Adhesive layer
3 Elastomer film
4 Supporting film
5 Cut
A Adhesive sheet for application on skin

DETAILED DESCRIPTION OF THE INVENTION

Figure 2:
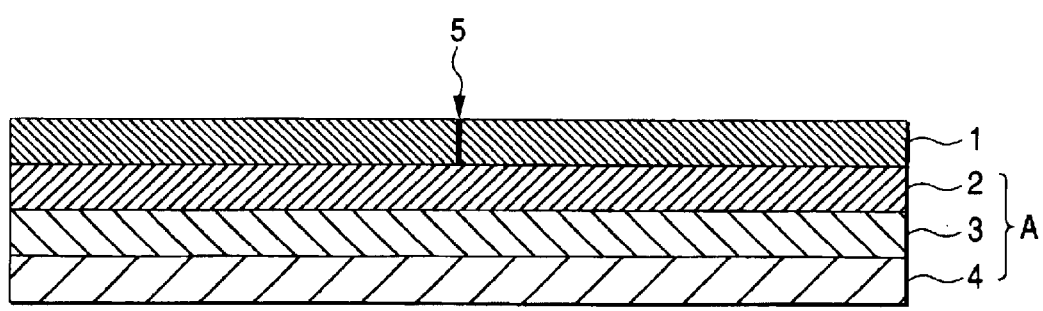
FIG. 2 is a schematic sectional view taken along the line X—X of FIG. 1.

Firstly, an example of the structure and use of the adhesive sheet for application on skin of the invention will be described in connection with FIGS. 1 and 2. As shown in FIG. 2, an adhesive sheet A of the invention contains a three-layer structure having a supporting film 4, an elastomer film 3 and an adhesive layer 2 laminated in this order. The adhesive layer 2 and the supporting film 4 have a component liquid or pasty at ordinary temperature present therein. The term "a component liquid or pasty at ordinary temperature is present in the supporting film" as used herein is also meant to indicate that the component liquid or pasty at ordinary temperature is present only in the surface of the supporting film on the elastomer film side thereof. It is preferred that the adhesive sheet A for application on skin of the invention be kept coated with a release paper 1 which has been treated with silicone or the like on the surface of the adhesive layer 2 until shortly before use in order to prevent the contamination on the surface of the adhesive layer. More preferably, the release paper is provided with a cut 5 to facilitate its release. Referring to the use of the adhesive sheet, the release paper 1 is firstly peeled off the adhesive sheet A. The adhesive sheet is then stuck to the skin on the side of the adhesive layer 2 thereof. The supporting film 4 is then removed from the adhesive sheet A. The adhesive sheet having such a structure and use can fairly follow the contour of the skin. The adhesive sheet of the invention has an elastomer film reinforced by a supporting film before sticking and thus exhibits an excellent handleability.

Examples of the production process and constituents of the adhesive sheet of the invention will be further described hereinafter. The term "ordinary temperature and humidity" as used herein is meant to indicate "23° C. and 60% RH", respectively.

The adhesive sheet for application on skin as disclosed herein is prepared normally by a process which contains preparing a laminated film of elastomer film and supporting film (hereinafter referred to as "laminated film"), and then forming an adhesive layer containing a component liquid or pasty at ordinary temperature on the elastomer film side of the laminated film. Specific examples of the process for the preparation of the laminated film include a melt extrusion process using T-die or inflation die, a process which contains casting the solution and then drying the coat, and a calender roll process. In the case where the surface of the supporting film is subjected to corona discharge treatment as described later during the preparation of the laminated film, it is preferred that the elastomer film be formed by the aforementioned process on the supporting film which has been previously prepared. Examples of the process for forming an adhesive layer on the elastomer film side of the laminated film thus prepared include a process which contains applying an adhesive directly to the surface of an elastomer film, and a process which contains forming an adhesive layer on a release paper, and then laminating the release paper with a laminated film in such an arrangement that the adhesive layer side of the release paper and the elastomer film side of the laminated film are opposed to each other. The adhesive sheet for application on skin of the invention thus prepared can be simply stuck to the skin while in a spirally-wound roll or predetermined form obtained by punching. In order to further enhance the handleability of the adhesive sheet, the adhesive sheet may be provided with a so-called half cut formed by partly cutting any of the supporting film and the release paper. Alternatively, both the supporting film and release paper may be partly cut and removed.

The elastomer film of the adhesive sheet of the invention exhibits flexibility and moisture permeability to exert an effect of fairly following the contour of the skin during sticking and lessening the irritation of the skin. It is essential that the adhesive sheet of the invention have a component liquid or pasty at ordinary temperature present in the adhesive layer and the supporting film. More preferably, the elastomer film has the component liquid or pasty at ordinary temperature present therein which has moved thereto. The elastomer film is specifically limited so far as it is so flexible as to follow even the contour of the skin. Examples of the elastomer employable herein include polyethylene, polyvinyl chloride, ethylene-vinyl acetate copolymer, polyamide, polyester, polyurethane, and acrylic polymer. Particularly preferred among these elastomers are polyamide, polyester, polyurethane and acrylic polymer, which have a high permeability to water vapor, because they cannot impede the perspiration from the skin. The thickness of the elastomer film is preferably predetermined to be from 10 $\mu$m to 150 $\mu$m, more preferably from 20 $\mu$m to 70 $\mu$m. When the thickness of the elastomer film falls below 10 $\mu$m, it is likely that the resulting film can break during peeling. On the contrary, when the thickness of the elastomer film exceeds 150 $\mu$m, it is likely that the resulting adhesive sheet can less fairly follow the contour of the skin or exhibits deteriorated permeability to water vapor. Referring to the mechanical physical properties of the elastomer film, the modulus of the elastomer film at 50% elongation is preferably predetermined to be from 0.2 to 15 N/mm$^2$ as measured at ordinary temperature and humidity by a tensile test from the standpoint of flexibility that allows the adhesive sheet to follow the contour of the skin.

The supporting film of the invention is laminated on the elastomer film to reinforce the flexible elastomer, improving the producibility and handleability of the adhesive sheet. The supporting film is preferably transparent or semi-transparent taking into account visibility that allows the confirmation of sticking site in use. Further, the supporting film normally has a relatively high elastic modulus with respect to the elastomer film. The modulus of the supporting film at 50% elongation is preferably from 2 to 200 N/mm$^2$, more preferably from 8 to 50 N/mm$^2$ as measured at ordinary temperature and humidity by a tensile test. The elastic modulus of the supporting film is properly determined by the elastic modulus of the elastomer film but is normally from about 3 to 20 times that of the elastomer film. It is appropriate that the supporting film has been previously subjected to various treatments on the side thereof on which the elastomer film is to be laminated because it is necessary that the elastomer film be laminated properly kept adhesive to the supporting film. Examples of these treatments include corona discharge, plasma treatment, and ultraviolet treatment.

Examples of the material to be used as supporting film include polyolefin such as polyethylene and polypropylene, polyester such as polyethylene terephthalate, polyamide such as nylon, polyvinyl chloride, and polyvinylidene chloride. The supporting film may be a composite film containing such a single film laminated with paper, nonwoven cloth, woven cloth, knitted cloth or metal foil in addition to such a single film. As the supporting film there is preferably used a polyolefin or polyester film from the standpoint of visibility or cost.

As the adhesive layer to be formed on the elastomer film side of the adhesive sheet for application on skin of the invention there may be used an adhesive mainly containing an acrylic polymer having a low irritation against the skin and an excellent transparency, the water vapor permeability of which can be highly predetermined. Specific examples of these acrylic polymers include those obtained by the copolymerization of a monomer such as (meth)acrylic acid alkyl ester (e.g., ethyl (meth)acrylate, propyl (meth)acrylate, butyl (meth)acrylate, hexyl (meth)acrylate, octyl (meth)acrylate, nonyl (meth)acrylate, decyl (meth)acrylate) which is a main component with one or more of hydrophilic monomers such as (meth)acrylic acid, itaconic acid, maleic acid, hydroxyethyl (meth)acrylate, methoxyethyl (meth)acrylate, ethoxyethyl (meth)acrylate, butoxyethyl (meth)acrylate and ethylene glycol (meth)acrylate. The term "(meth)acrylate" as used herein is meant to indicate both acrylate and methacrylate and the term "(meth)acrylic acid" as used herein is meant to indicate both acrylic acid and methacrylic acid. The thickness of the adhesive layer is preferably from 10 μm to 100 μm from the standpoint of adhesivity to the skin, flexibility that allows the adhesive sheet to follow the contour of the skin and permeability to water vapor. The adhesive layer is preferably subjected to crosslinking by treatment with a heat-crosslinking agent-such as isocyanate compound, organic peroxide, epoxy group-containing compound and metal chelate compound or treatment by ultraviolet rays, γ-rays, electron rays or the like to improve the adhesivity thereof.

In the adhesive sheet for application on skin of the invention, the component liquid or pasty at ordinary temperature to be incorporated in the adhesive layer plays an important role of adjusting the adhesion between the elastomer film and the supporting film. Referring further to an example, when the aforementioned adhesive containing a component liquid or pasty at ordinary temperature is applied to the laminated film on the elastomer film side thereof during the preparation of the adhesive sheet for application on skin of the invention, the component liquid or pasty at ordinary temperature in the adhesive layer partly moves to the supporting film through the elastomer film, attaining substantial equilibrium, with the elapse of about 24 hours at ordinary temperature. This phenomenon causes the adhesion between the elastomer film and the supporting film to be deteriorated, making it possible for the elastomer film and the supporting film, which has been stuck fast to each other during preparation, to be peelable off each other in use.

The component liquid or pasty at ordinary temperature is specifically limited so far as it is compatible with the acrylic polymer. Examples of the component liquid or pasty at ordinary temperature employable herein include esters of phthalic acid, maleic acid, adipic acid, stearic acid or various aliphatic acids with alkyl alcohol or polyhydric alcohol such as ethylene glycol and glycerin. Specific examples of these esters include esters of monohydric alcohol such as dibutyl phthalate, di-2-ethylhexyl phthalate, dibutyl adipate, di-2-ethylhexyl sebacate, dibutyl maleate, ethyl myristate, isopropyl myristate, isopropyl palmitate, butyl stearate, isopropyl isostearate, hexyl laurate, cetyl lactate, myristyl lactate, diethyl phthalate, octyldodecyl myristate, octyldodecyl oleate, hexyldodecyl dimethyloctanate, cetyl 2-ethylhexanate, isocetyl 2-ethylhexanate, stearyl 2-ethylhexanate and dioctyl succinate, and esters of dihydric or higher alcohol such as propylene glycol dicaprylate, propylene glycol dicaprate, propylene glycol diisostearate, glyceryl monocaprylate, glyceryl tricaprylate, glyceryl tri-2-ethylhexanate, glyceryl tricaprate, glyceryl trilaurate, glyceryl triisostearate, glyceryl trioleate and trimethylolpropane tri-2-ethylhexanate. These compounds may be used singly or in combination of two or more thereof. The component liquid or pasty at ordinary temperature can be properly determined by other factors of the adhesive sheet. From the standpoint of the compatibility with the acrylic adhesive, there may be preferably used carboxylic acid ester, more preferably glycerin aliphatic acid ester. The content of the component liquid or pasty at ordinary temperature varies with the kind of the adhesive, elastomer film and component liquid or pasty at ordinary temperature but normally is from 20 to 200 parts by weight based on 100 parts by weight of the adhesive or from 5 to 30 g/m² as basic weight.

The degree of the drop of adhesion between the elastomer film and the supporting film, which is a feature of the adhesive sheet for application on skin of the invention, will be described in detail hereinafter with reference to peeling strength of elastomer film and supporting film. The appropriate peeling strength of the elastomer film and supporting film before the formation of the adhesive layer is normally from 1.5 to 10 N/20 mm from the standpoint of workability during production. The component liquid or pasty at ordinary temperature in the adhesive layer partly moves to the supporting film through the elastomer film, resulting in the drop of the aforementioned peeling strength to a range of from about 0.08 to 1.0 N/20 mm. The cause of the phenomenon of drop of adhesion between the elastomer film and the supporting film is not necessarily obvious. It is presumed that the component liquid or pasty at ordinary temperature in the adhesive layer partly moves to the supporting film through the elastomer film with time, forming an extremely weak border layer (WBL) at the border of the elastomer film with the supporting film. The movement of the component liquid or pasty at ordinary temperature is preferably from 0.1 to 5 g/m² per unit area of the supporting film. When the movement of the component liquid or pasty at ordinary temperature falls below 0.1 g/m², the desired effect of lowering the adhesion between the elastomer film and the supporting film can be difficultly obtained. On the contrary, when the movement of the component liquid or pasty at ordinary temperature exceeds 5 g/m², the adhesion between the two films decreases more than required, not only making it likely that the supporting film can be partly peeled off the elastomer film during the storage of the adhesive sheet but also giving a tendency that the adhesive containing the component liquid or pasty at ordinary temperature is deteriorated also in its adhesivity and hence in its practicality until the movement exceeds the above defined range.

The range of movement of the component liquid or pasty at ordinary temperature to the supporting film can be adjusted by the content and kind of the component liquid or pasty at ordinary temperature and the thickness and kind of the adhesive and elastomer film. In order to control the movement of the component liquid or pasty at ordinary temperature to the supporting film within an even more desirable range, it is preferably arranged such that an adhesive made of an acrylic polymer containing a carboxylic acid ester incorporated therein in an amount of from 20 to 200 parts by weight based on 100 parts by weight of the adhesive or from 5 to 30 g/m² as basic weight as a component liquid or pasty at ordinary temperature be applied to one side of an elastomer film having a thickness of from 10 μm to 150 μm made of polyamide, polyester, polyurethane, acrylic polymer or the like to a dry thickness of from 10 μm to 100 μm.

While the aforementioned description has been made with reference to the technique which can overcome the disadvantages of the conventional techniques by allowing a component liquid or pasty at ordinary temperature to act as a component moving from the adhesive layer and be present in both the adhesive layer and supporting film, solution can be given by the following other techniques. For example, an adhesive layer may be formed on a laminated film made of a supporting film and an elastomer film either or both of which have a component liquid or pasty at ordinary temperature incorporated therein on the elastomer film side thereof to form an adhesive sheet for application on skin.

The adhesive sheet for application on skin of the invention has the aforementioned arrangement and thus allows the supporting film and the elastomer film to be easily peeled off each other. The adhesive sheet having a component liquid or pasty at ordinary temperature present in both the adhesive layer and the supporting film as a moving component exerts an excellent effect in both workability and handleability. In other words, the elastomer film and the supporting film can be prevented from being peeled off each other during production. Further, the supporting film can be easily removed from the elastomer film in use.

The invention will be further described in the following examples, but the invention should not be construed as being limited thereto. Various applications of the invention can be made so far as they do not depart from the technical scope of the invention. The term "%" and "parts" as used hereinafter are meant to indicate "% by weight" and "parts by weight", respectively.

EXAMPLE 1

A polyether polyurethane (RESAMINE P-210, produced by Dainichiseika Color & Chemicals Mfg. Co., Ltd.) as an elastomer resin was heat-melted in a twin-screw kneader, and then extruded through a T-die extruder to a thickness of 30 μm to form an elastomer film. Subsequently, the elastomer film was stuck fast to a stretched polypropylene film (SILFAN MT (thickness: 40 μm), produced by GUNZE LTD.) which had been subjected to corona discharge treatment to have a surface tension of 420 N/mm as measured with a wet index solution as a supporting film on the corona-discharged surface thereof by means of a rubber roll to obtain a laminated film containing an elastomer film and a supporting film.

Subsequently, 100 parts (by solid content) of a solvent type acrylic adhesive mainly composed of a copolymer made of isononyl acrylate, 2-methoxyethyl acrylate and acrylic acid in a weight proportion of 65:30:5 were blended with 60 parts of triisoglyceride caprylate as a component liquid or pasty at ordinary temperature. The mixture was then subjected to heat crosslinking with an isocyanate-based compound to obtain an adhesive. The adhesive thus obtained was then applied to a release paper to a dry thickness of 30 μm. The release paper and the laminated film were then laminated by means of a rubber roll in such an arrangement that the adhesive layer side of the release paper and the elastomer film side of the laminated film were opposed to each other. The laminated material was then kept at a temperature of 60° C. for 24 hours to obtain an adhesive sheet for application on skin with a release paper.

EXAMPLE 2

An adhesive sheet for application on skin with a release paper was obtained in the same manner as in Example 1 except that as the elastomer resin there was used a polyether polyurethane (ELASTRAN OH3-37, produced by BASF POLYURETHANE ELASTOMER CO., LTD.) and the amount of triglyceride caprylate was 50 parts.

EXAMPLE 3

An adhesive sheet for application on skin with a release paper was obtained in the same manner as in Example 1 except that the amount of triglyceride caprylate was 100 parts.

EXAMPLE 4

An adhesive sheet for application on skin with a release paper was obtained in the same manner as in Example 1 except that the amount of triglyceride caprylate was 30 parts.

EXAMPLE 5

An adhesive sheet for application on skin with a release paper was obtained in the same manner as in Example 1 except that the amount of triglyceride caprylate was 10 parts.

EXAMPLE 6

An adhesive sheet for application on skin with a release paper was obtained in the same manner as in Example 1 except that the amount of triglyceride caprylate was 5 parts.

EXAMPLE 7

An adhesive sheet for application on skin with a release paper was obtained in the same manner as in Example 1 except that the supporting film was subjected to corona discharge treatment to have a surface tension of 500 N/mm as measured with a wet index solution.

EXAMPLE 8

An adhesive sheet for application on skin with a release paper was obtained in the same manner as in Example 1 except that 60 parts of triglyceride caprylate were replaced by 60 parts of isopropyl myristate.

COMPARATIVE EXAMPLE 1

An adhesive sheet for application on skin with a release paper was obtained in the same manner as in Example 1 except that triglyceride caprylate was not added.

The properties of the laminated films and adhesive sheets obtained in Examples 1 to 8 and Comparative Example 1 are set forth in Table 1 below. The definition of terms and the method for evaluation of properties will be described below.

<A> Amount of Component Liquid or Pasty at Ordinary Temperature (The Term "Component Liquid or Pasty at Ordinary Temperature" is Omitted in Table 1)

(a-1) Content

The content of the component liquid or pasty at ordinary temperature in the adhesive layer shortly after the preparation of the adhesive sheet with a release paper obtained in Examples 1 to 8 and Comparative Example 1 (i.e., when the component liquid or pasty at ordinary temperature is not present in the supporting film) was calculated as follows. Firstly, from the basic weight j of the adhesive layer determined by the specific gravity h of the adhesive layer and the thickness i of the adhesive layer and the mixing ratio of the adhesive and the moving component portion (k and l, respectively) was determined the content m of the component liquid or pasty at ordinary temperature in the adhesive layer per unit area by the following equation:

$$h(-) \times 10^6 (g/m^3) \times i(m) = j(g/m^2)$$

$$j(g/m^2) \times k(parts)/(k+1)(parts) = m(g/m^2)$$

(a-2) Movement

The content of the component liquid or pasty at ordinary temperature present in the supporting film after the movement of the component liquid or pasty at ordinary temperature to the supporting film in the adhesive sheet with a release paper obtained in Examples 1 to 8 and Comparative Example 1 was measured as follows. Firstly, the release paper was peeled off the adhesive sheet with a release paper which had been stored at a temperature of 60° C. for 24 hours after preparation. The supporting film was then peeled off the elastomer film. The supporting film thus peeled was slit into a strip having a size of 30 mm×50 mm which was then dipped in 50 cc of ethyl acetate at ordinary temperature for 24 hours so that it was extracted. The extract thus obtained was then injected into a capillary glass chromatography analyzer. From the resulting peak area of chromatogram was then determined the amount of the component liquid or pasty at ordinary temperature which had moved to the supporting film. In order to peel the supporting film off the elastomer film, the adhesive sheet off which the release paper had been peeled was stuck to an aluminum plate. Subsequently, the supporting film was peeled off the elastomer film.

<B> Peel Force (b-1) Before the Formation of Adhesive Layer

The peel force between the elastomer film and the supporting film before the formation of the adhesive layer (i.e., adhesion between the elastomer film and the supporting film developed when the component liquid or pasty at ordinary temperature is not present in the supporting film) in the laminated films obtained in Examples 1 to 8 and Comparative Example 1 was measured as follows. In some detail, a commercial available double-sided adhesive tape was stuck to the surface of the elastomer film. The laminate was slit into a strip having a size of from 20 mm×100 mm which was then stuck and fixed to an aluminum plate. Subsequently, the force required to peel the supporting film off the elastomer film by grasping the end of the supporting film of the laminated film stuck and fixed to the aluminum plate and pulling it at an angle of 90 degrees at a rate of 300 mm/min was measured at ordinary temperature and humidity by means of a tensile testing machine.

<C> Producibility

The adhesive sheet with a release paper obtained in Examples 1 to 8 and Comparative Example 1 were each then evaluated for producibility in the following manner. In some detail, the laminated film was slit into a strip having a size of 200 mm×600 mm. The laminated film was then laminated with the release paper in such an arrangement that the elastomer film side of the laminated film and the adhesive layer side of the release paper were opposed to each other by means of a rubber roll. Those showing no lifting of the supporting film off the elastomer film during this procedure are evaluated as good. Those showing any lifting of the supporting film off the elastomer film during this procedure are evaluated as poor.

<D> Handleability

The adhesive sheets with release paper obtained in Examples 1 to 8 and Comparative Example 1 were each evaluated for handleability in use as follows. In some detail, the adhesive sheet with a release paper was cut into a strip having a size of 50 mm×50 mm. The release paper was removed from the adhesive sheet. The adhesive sheet was then stuck to the inner side of the forearm. Shortly after sticking, the supporting film was peeled off with fingers. The ease of peeling of the supporting film off the elastomer film during this procedure was then evaluated in accordance with the following criterion. Those which can be easily peeled are evaluated as excellent. Those which can be peeled are evaluated as good. Those which are stuck to the elastomer film so fast that they can be difficultly peeled are evaluated as poor.

TABLE 1

|  | <A> Content (g/m²) | | <B> Peel force (N/20 mm) | | Producibility <C> | Handleability <D> |
|  | Content (a-1) | Movement (a-2) | Before the formation of adhesive layer (b-1) | After the formation of adhesive layer (b-2) | | |
| --- | --- | --- | --- | --- | --- | --- |
| Example 1 | 11.2 | 1.2 | 3.6 | 0.25 | Good | Excellent |
| Example 2 | 10.2 | 1.3 | 2.4 | 0.13 | Good | Excellent |
| Example 3 | 15.2 | 1.5 | 3.6 | 0.19 | Good | Excellent |
| Example 4 | 6.9 | 0.9 | 3.6 | 0.39 | Good | Excellent |
| Example 5 | 2.7 | 0.3 | 3.6 | 0.57 | Good | Excellent |
| Example 6 | 1.4 | 0.2 | 3.6 | 1.73 | Good | Good |
| Example 7 | 11.2 | 1.1 | 9.7 | 0.45 | Good | Excellent |
| Example 8 | 11.2 | 0.7 | 3.6 | 0.24 | Good | Excellent |
| Comparative Example 1 | 0 | 0 | 3.6 | 2.8 | Good | Poor |

(b-2) After the Formation of Adhesive Layer

The peel force between the elastomer film and the supporting film after the formation of the adhesive layer (i.e., adhesion between the elastomer film and the supporting film developed when the component liquid or pasty at ordinary temperature is present in the supporting film) in the adhesive sheets with a release paper obtained in Examples 1 to 8 and Comparative Example 1 was measured as follows. In some detail, the adhesive sheet with a release paper which had been stored at a temperature of 60° C. for 24 hours after preparation was slit into a strip having a size of 20 mm×100 mm. The release paper was then peeled off the adhesive sheet. The adhesive sheet was then stuck and fixed to an aluminum plate having a smooth surface. The adhesive sheet was then measured for peel force in the same manner as in (b-1).

While the invention has been described in detail and with reference to specific embodiments thereof, it will be apparent to one skilled in the art that various changes and modifications can be made therein without departing from the spirit and scope thereof.

What is claimed is:

1. An adhesive sheet for application on skin which comprises an adhesive layer and a laminated film comprising an elastomer film having provided on one side thereof a supporting film, said adhesive layer being formed on the elastomer film side of the laminated film, wherein the adhesive layer mainly comprises an acrylic polymer and both the adhesive layer and the supporting film comprise a component compatible with the acrylic polymer that is liquid or pasty at ordinary temperature.

2. The adhesive sheet for application on skin according to claim 1, wherein the supporting film is peelably formed on one side of the elastomer film.

3. The adhesive sheet for application on skin according to claim 2, which is stuck to an adherend on the adhesive layer side thereof, and then causes the supporting film to be peeled off the elastomer film before use.

4. The adhesive sheet for application on skin according to claim 1, wherein the elastomer film is made of an elastomer selected from the group consisting of polyester polyurethane, polyether polyurethane, polyether polyester and polyether polyamide.

5. The adhesive sheet for application on skin according to claim 1, wherein the thickness of the elastomer film is from 10 μm to 150 μm.

6. The adhesive sheet for application on skin according to claim 1, wherein the supporting film is made of a polymer selected from the group consisting of polyethylene, polypropylene and polyester.

7. The adhesive sheet for application on skin according to claim 1, wherein the thickness of the supporting film is from 5 μm to 120 μm.

8. The adhesive sheet for application on skin according to claim 1, wherein the supporting film has been previously subjected to at least one treatment selected from the group consisting of corona discharge, plasma treatment, and ultraviolet treatment on the side thereof on which the elastomer film is to be laminated.

9. The adhesive sheet for application on skin according to claim 1, wherein the supporting film is transparent or semi-transparent.

10. The adhesive sheet for application on skin according to claim 1, wherein the content of the component compatible with the acrylic polymer that is liquid or pasty at ordinary temperature in the supporting film is from 0.1 to 5 g/m$^2$.

11. The adhesive sheet for application on skin according to claim 1, wherein the component compatible with the acrylic polymer that is liquid or pasty at ordinary temperature is a carboxylic acid ester.

12. The adhesive sheet for application on skin according to claim 11, wherein the component compatible with the acrylic polymer that is liquid or pasty at ordinary temperature is a glycerin aliphatic acid ester.

13. The adhesive sheet for application on skin according to claim 11, wherein the component liquid or pasty at ordinary temperature is selected from the group consisting of propylene glycol dicaprylate, propylene glycol dicaprate, propylene glycol diisostearate, glyceryl monocaprylate, glyceryl tricaprylate, glyceryl tri-2-ethylhexanate, glyceryl tricaprate, glyceryl trilaurate, glyceryl triisostearate, glyceryl trioleate, trimethylolpropane tri-2-ethylhexanate and isopropyl myristate.

14. The adhesive sheet for application on skin according to claim 1, wherein the adhesive layer is subjected to crosslinking by treatment with a heat-crosslinking agent selected from the group consisting of an isocyanate compound, an organic peroxide, an epoxy group-containing compound and a metal chelate compound or treatment by rays selected from the group consisting of ultraviolet rays, γ-rays that is electron rays.

15. A process for the production of an adhesive sheet for application on skin, which adhesive sheet comprises an adhesive layer and a laminated film comprising an elastomer film having provided on one side thereof a supporting film, said adhesive layer being formed on the elastomer film side of the laminated film, wherein the adhesive layer comprises a polymer and both the adhesive layer and the supporting film comprise a component compatible with the polymer and liquid or pasty at ordinary temperature, which process for the production of the adhesive sheet comprises applying an adhesive comprising the component liquid or pasty at ordinary temperature to the laminated film, and then allowing a part of the liquid or pasty component comprised in the adhesive to move toward the supporting film so that it is present therein.

16. The process for the production of an adhesive sheet for application on skin according to claim 15, wherein the polymer constituting the adhesive is a polymer mainly comprising an acrylic polymer.

17. A process for the production of an adhesive sheet for application on skin, which adhesive sheet comprises an adhesive layer and a laminated film comprising an elastomer film having provided on one side thereof a supporting film, said adhesive layer being formed on the elastomer film side of the laminated film, wherein the adhesive layer comprises a polymer and both the adhesive layer and the supporting film comprise a component compatible with the polymer that is liquid or pasty at ordinary temperature, which process for the production of the adhesive sheet comprises forming the adhesive layer on the laminated film made of the supporting film and the elastomer film either or both of which have a component liquid or pasty at ordinary temperature incorporated therein on the elastomer film side thereof, and then allowing a part of the liquid or pasty component comprised in either or both of the supporting film and the elastomer film to move toward the adhesive layer.

18. The process for the production of an adhesive sheet for application on skin according to claim 17, wherein the polymer constituting the adhesive is a polymer mainly comprising an acrylic polymer.

* * * * *